United States Patent
Maruyama (10) Patent No.: US 7,384,766 B2
(45) Date of Patent: Jun. 10, 2008

(54) GENE-SUBSTITUTED MICROORGANISMS, AND PRODUCTION METHOD OF POLYESTERS USING THE SAME

(75) Inventor: Hiroyuki Maruyama, Kakogawa (JP)

(73) Assignees: Kaneka Corporation, Osaka (JP); The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/492,756

(22) Filed: Jul. 26, 2006

(65) Prior Publication Data

US 2008/0038801 A1 Feb. 14, 2008

(51) Int. Cl.
 *C12N 1/20* (2006.01)
 *C12P 21/06* (2006.01)
(52) U.S. Cl. .................. 435/69.1; 435/252.3
(58) Field of Classification Search ............ 435/252.3, 435/69.1
 See application file for complete search history.

(56) References Cited

U.S. PATENT DOCUMENTS

| 5,981,257 | A | 11/1999 | Fukui et al. |
| 6,593,116 | B1 | 7/2003 | Huisman et al. |
| 2005/0009949 | A1 | 1/2005 | Doi et al. |
| 2006/0160195 | A1 | 7/2006 | Ono et al. |

FOREIGN PATENT DOCUMENTS

| JP | 57-150393 | 9/1982 |
| JP | 9-205983 | 11/1984 |
| JP | 59-205983 | 11/1984 |
| JP | 59-220192 | 12/1984 |
| JP | 5-93049 | 4/1993 |
| JP | 7-265065 | 10/1995 |
| JP | 10-108682 | 4/1998 |
| JP | HEI10-108682 | 4/1998 |
| JP | 2001-340078 | 12/2001 |
| JP | 2005-333933 | 12/2005 |
| MY | PI 20051576 | 8/2005 |
| MY | PI20051576 | 8/2005 |
| WO | WO 03/050277 A1 | 9/2002 |
| WO | WO 2004/074476 A1 | 1/2004 |
| WO | WO 2005/098001 A1 | 8/2005 |

OTHER PUBLICATIONS

Mikayama et al, Molecular cloning and functional expression of a cDNA encoding glycosylation-inhibiting factor, 1993, PNAS, vol. 90, pp. 10056-10060.*
Rudinger et al, Characteristics of the amino acids as components of a peptide hormone sequence, 1976, Peptide Hormones, Biological Council, pp. 1-7.*
York et al, Accumulation of the PhaP Phasin of Ralstonia eutrpha is dependent on production of polyhydroxybutyrate in cells, 2001, J Bacteriology, vol. 183, pp. 4217-4226.*
Fukui et al, Cloning and analysis of the poly (3-Hydroxybutyrate-co-3Hydroxyhexanoate) biosynthesis genes of Aeromonas caviae, 1997, J Bacteriology, vol. 179, pp. 4821-4830.*
Kichise, et al, Applied and Environmental Microbiology, May 2002, pp. 2411-2419.
Search Report dated May 16, 2006 for Related International Application No. PCT/JP2006/303140 (now abandoned).
Search Report dated Oct. 10, 2006 for Related International Application No. PCT/JP2006/314498.
Kichise, et al, Applied and Environmental Microbiology, May 2002, pp. 2411 - 2419.

* cited by examiner

*Primary Examiner*—Mark Navarro
(74) *Attorney, Agent, or Firm*—Sughrue Mion, PLLC (57) ABSTRACT

The present invention provides a recombinant microbial strain capable of stably producing a polyhydroxyalkanoic acid (PHA) at a high production rate in an industrial fermentation process. The present invention also relates to a recombinant microbial strain prepared by substituting an exogenous polyhydroxyalkanoic acid synthase gene for a polyhydroxyalkanoic acid synthase gene on the chromosome of the microorganism.

8 Claims, 2 Drawing Sheets

GENE-SUBSTITUTED MICROORGANISMS, AND PRODUCTION METHOD OF POLYESTERS USING THE SAME

TECHNICAL FIELD

The present invention relates to an improved microbial strain useful for an industrial production of a polyhydroxyalkanoic acid (PHA), which is a biodegradable polyester, and a production method of PHA using the same.

BACKGROUND ART

Polyhydroxyalkanoic acids are polyester-type organic polymers produced by a wide range of microorganisms. These polymers are biodegradable, are thermoplastic polymers, and are producible from recyclable resources, so that attempts for an industrial production of the polymers as environment-conscious materials or biocompatible materials to be used for various industries have been conducted.

The monomer constituting said polyester is 3-hydroxyalkanoic acid in the general name. Specifically, its polymer molecule is formed by homopolymerization or copolymerization of 3-hydroxybutyric acid, 3-hydroxyvaleric acid, 3-hydroxyhexanoic acid, 3-hydroxyoctanoic acid, or 3-hydroxyalkanoic acid having a longer alkyl chain. Poly 3-hydroxybutyric acid (hereinafter referred to briefly as "P(3HB)"), which is a homopolymer of 3-hydroxybutyric acid (hereinafter referred to briefly as "3HB"), was first discovered in *Bacillus megaterium* in 1925. However, since P(3HB) is high in crystallinity, it is hard and brittle, so that the range of practical application thereof is limited. Therefore, studies have been undertaken to improve these properties.

Among others, a process for producing a copolymer made of 3-hydroxybutyric acid (3HB) and 3-hydroxyvaleric acid (3HV) (hereinafter such copolymer is referred to briefly as P(3HB-co-3HV)) is disclosed (for example, refer to Japanese Kokai Publication Sho-57-150393 and Japanese Kokai Publication Sho-59-220192). This P(3HB-co-3HV) is rich in flexibility as compared with P(3HB), hence was expected to have a broader application range. In actuality, however, P(3HB-co-3HV) shows only slight changes in physical properties even when the molar fraction of 3HV is increased. In particular, the flexibility can not be improved. Thus, it has been used only in the field of rigid shaped articles such as shampoo bottles and disposable razor grips.

Moreover, a medium-chain PHA constituted of 3-hydroxyalkanoic acids having 6 to 16 carbon atoms is known to be in lower crystallinity as compared with P(3HB) or P(3HB-co-3HV), and rich in elasticity (refer to Madison et al., Microbiol. Mol. Biol. Rev., 63:21-53 (1999)). Thus, applications for different fields are hoped for. Studies for producing the medium-chain PHA has been conducted by introducing a PHA synthase gene of the genus *Pseudomonas* into the genus *Pseudomonas,* the genus *Ralstonia,* or *Escherichia coli,* but all of these processes were not suitable for the industrial production due to low productivity (refer to Matsusaki et al., J. Bacteriol., 180:6459-6467 (1998); Matsusaki et al., Appl. Micrbiol. Biotechnol., 53:401-409 (2000); and Langenbach et al., FEMS Microbiol. Lett., 150:303-309 (1997)).

In recent years, studies have been made concerning the copolymer consisting of two components 3HB and 3-hydroxyhexanoic acid (hereinafter referred to as 3HH for short) (hereinafter such copolyesters are referred to as P(3HB-co-3HH) for short) and the process for producing it (refer to Japanese Kokai Publication Hei-05-93049 and Japanese Kokai Publication Hei-07-265065). According to these patent documents, this process for producing P(3HB-co-3HH) comprises fermentative production thereof from fatty acids, such as oleic acid, or oils and fats, such as olive oil, using *Aeromonas caviae* isolated from soil. Studies concerning the properties of P(3HB-co-3HH) have also been made (refer to Doi et al., Macromolecules, 28:4822-4828 (1995)). According to this report, when *Aeromonas caviae* is cultured using fatty acids of not less than 12 carbon atoms as the only carbon source, P(3HB-co-3HH) with a 3HH composition of 11 to 19 mole percent can be fermentatively produced. It has been revealed that the properties of such P(3HB-co-3HH) change from hard and brittle gradually to soft and flexible, to an extent exceeding the flexibility of P(3HB-co-3HV), with the increase in the 3HH composition. That is, P(3HB-co-3HH) can be given a wide applicable range of physical properties, from properties of rigid polyesters to properties of flexible polyesters, by changing the 3HH composition and therefore can be expected to be applicable in a wide range, from a chassis for a TV-set and the like, for which rigidity is required, to films and the like, for which flexibility is required. However, with this production process, the productivity of polyester was as low as the cell production of 4 g/L and polyester content of 30%, and the process has yet to be said insufficient as the process for the practical use of the polyester. Therefore, a process providing higher productivity has been searched for toward the practical use.

Attempts aiming at the industrial production of P(3HB-co-3HH) have also been conducted. Among cultures using *Aeromonas hydrophila,* in a 43-hour feed culture using oleic acid as a carbon source, P(3HB-co-3HH) with the cell productivity of 95.7 g/L, polyester content of 45.2% and 3HH composition of 17% was produced (refer to Lee et al., Biotechnol. Bioeng., 67:240-244 (2000)). Furthermore, *Aeromonas hydrophila* was cultured using glucose and lauric acid as carbon sources, and the cell productivity of 50 g/L and polyester content of 50% were attained (refer to Chen et al., Appl. Microbiol. Biotechnol., 57:50-55 (2001)). However, *Aeromonas hydrophila* has pathogenicity to human (refer to "Safety Control Regulations on Pathogen, etc." issued by National Institute of Infectious Diseases; attached table 1, appended chart 1 (1999)), and thus cannot be said as a suitable species for the industrial production. Moreover, since expensive carbon sources are used in these culture productions, use of a cheap carbon source has also been asked for in view of the production cost.

Therefore, attempts for the production using a safe host and improvement of the productivity have been conducted. A polyhydroxyalkanoic acid (PHA) synthase gene was cloned from *Aeromonas caviae* (refer to Japanese Kokai Publication Hei-10-108682; and Fukui et al., J. Bacteriol., 179:4821-4830 (1997)). As a result of producing P(3HB-co-3HH) using a transformant prepared by introducing this gene into *Ralstonia eutropha* (formerly *Alcaligenes eutrophus*), the cell productivity was 4 g/L and the polyester content was 30%. Moreover, as a result of culturing this transformant using a vegetable oil as a carbon source, the cell productivity of 4 g/L and polyester content of 80% were attained (refer to Fukui et al., Appl. Microbiol. Biotecnol., 49:333-336 (1998)). Furthermore, researches on culture processes have also been conducted as can be seen in improvements of the cell productivity, polyester content and 3HH composition of up to 45 g/L, 62.5%, and 8.1%, respectively, by improving culture conditions (refer to Japanese Kokai Publication No. 2001-340078).

Moreover, *Ralstonia eutropha* capable of producing P(3HB-co-3HH) using fructose as a carbon source was also constructed, but this strain had low polyester productivity, and cannot be said to be suitable for the practical production (refer to Fukui et al., Biomacromolecules, 3:618-624 (2002)).

A P(3HB-co-3HH)-producing strain using *Escherichia coli* as the host was also constructed. A strain prepared by introducing a PHA synthase gene of the genus *Aeromonas*, NADP-acetoacetyl Co-A reductase gene of *Ralstonia eutropha*, or the like, into *Escherichia coli* was constructed. As a result of culturing said *Escherichia coli* using dodecane as a carbon source, the cell productivity of 79 g/L, polyester content of 27.2%, and 3HH composition of 10.8% were obtained (refer to Park et al., Biomacromolecules, 2:248-254 (2001)).

With the aim of improving the productivity of P(3HB-co-3HH) and controlling the 3HH composition, artificial modification of PHA synthase was carried out. Among PHA synthase mutants derived from *Aeromonas caviae*, a mutant enzyme in which serine is substituted for 149th amino acid asparagine and a mutant enzyme in which glycine is substituted for 171st aspartic acid showed improved PHA synthase activity in *Escherichia coli* and 3HH composition (refer to Kichise et al., Appl. Environ. Microbiol., 68:2411-2419 (2002)). Moreover, it was reported that a mutant enzyme in which isoleucine is substituted for 518th phenylalanine or a mutant enzyme in which glycine is substituted for 214th valine were improved in the PHA synthase activity in *Escherichia coli* and polyester content (refer to Amara et al., Appl. Microbiol. Biotechnol., 59:477-482 (2002)). However, since these mutants used particular *Escherichia coli* species as the host and still showed low polyester content, further improvements aiming at the industrial production making use of characteristics of these mutant enzymes have been required.

One of the most important subjects when PHAs are cultured in the industrial scale using a strain produced by applying recombinant DNA technologies is the stability of the transgene. For the gene transfer, a process comprising using a plasmid, a process comprising incorporation onto a host chromosome, and the like are used. However, a plasmid is known to be lost during proliferation and division of recombinant cells (refer to Japanese Kokai Publication Sho-59-205983). Therefore, cells from which a plasmid is lost lose PHA production ability, which leads to decrease of the commercial productivity. Conventionally, recombinant cells are generally cultured by selectively growing and retaining plasmid retention cells alone by adding antibiotics to a medium. However, problems such as a cost increase by the use of antibiotics, or influences to environment by residual antibiotics in a waste culture solution occur. Moreover, for stabilizing the plasmid, recombinant *Escherichia coli* prepared by introducing parB gene derived from R1 plasmid into P(3HB)-producing plasmid was produced (refer to Lee et al., J. Biotechnol., 32:203-211 (1994)). This *Escherichia coli* retained almost 100% of the plasmid even after culturing 110 to 120 generations. However, the plasmid still has the risk of being lost.

On the other hand, a gene incorporated onto a chromosome is thought to be stable. For this reason, a microorganism in which a gene involved with PHA synthesis was incorporated onto the chromosome was reported (refer to U.S. Pat. No. 6,593,116, Kranz et al., Appl. Environ. Microbiol., 63:3003-3009 (1997); and York et al., J. Bacteriol., 183:4217-4226 (2001)).

The *Escherichia coli* strain produced by randomly inserting a gene coding for a PHA biosynthesis enzyme onto the chromosome of *Escherichia coli*, as disclosed in U.S. Pat. No. 6,593,116, produced P(3HB) at the level exceeding 85% of the dry cell weight. However, for making *Escherichia coli* produce P(3HB-co-3HH) having superior practical physical properties, it is required to make genes for supplying a substrate monomer coexist, or to supply expensive fatty acids, etc., to a medium. These requirements prevent attaining higher production efficiency. Furthermore, when the gene is randomly incorporated onto the chromosome, depending on the site to be incorporated, expression of the gene on that site or on the peripheral site thereof may be affected, and sufficient performances as a PHA-producing strain cannot be exhibited.

In the case of introducing an exogenous PHA synthase gene into a host in the form of plasmid or incorporating the same onto the chromosome, when a microbial species which inherently produces a PHA, such as the genus *Ralstonia* or the genus *Pseudomonas*, is used as the host, the strain which lost the inherent ability to produce a PHA has been used. Since such a strain is produced through mutation operations, the proliferation ability or biological activity is inferior to that of the parental strain (refer to Schlegel et al., Arch. Mikrobiol., 71:283-294 (1970); Schubert et al., J. Bacteriol., 170:5837-5847 (1988); Peoples et al., J. Biol. Chem., 264: 15298-15303 (1989); and the like), and it is hard to say that such a strain exhibits sufficient production ability as the PHA-producing strain.

On the other hand, in the report in which a PHA synthase gene derived from *Chromatium vinosum* is substituted for a PHA synthase gene on the chromosome of *Ralstonia eutropha*, P(3HB) was accumulated at 91% to the dry cell weight, which exceeded wild strains (York et al., J. Bacteriol., 183:4217-4226 (2001)). However, the cell productivity was as low as 1.8 g/L, and also the produced polyester was hard and brittle P(3HB), not P(3HB-co-3HH) with which a wide range of applications can be expected. Thus, for the commercial production of the polyester, there still have remained subjects to be solved.

SUMMARY OF THE INVENTION

As mentioned above, there still have been a lot of subjects for the commercial production of PHA.

The present invention has for its object to provide a recombinant microbial strain capable of accumulating a copolyester with which a broad range of applications can be expected stably at a high level in a culture process in the industrial scale, and to provide a production method of a copolyester using the same.

DETAILED DESCRIPTION OF THE INVENTION

The present inventors made intensive investigations for solving the above subjects, and found that a polyester-producing microorganism prepared by substituting an exogenous polyhydroxyalkanoic acid synthase gene for a polyhydroxyalkanoic acid synthase gene on the chromosome can accumulate a PHA stably at a high level.

For stabilizing the synthesis of PHA, it has been suggested effective to introduce a gene onto the chromosome. However, effects obtained when the PHA synthase gene of a wild strain is site-specifically substituted with another PHA synthase gene to accumulate copolyesters by disrupting the preexisting gene and expressing the transgene at the same time has not been known yet. Moreover, it could not be anticipated simply from the technologies which have been conventionally known.

As shown in Examples, a microbial strain prepared by substituting a polyhydroxyalkanoic acid synthase mutant gene derived from *Aeromonas caviae* for a polyhydroxyalkanoic acid synthase gene on the chromosome of a *Ralstonia eutropha* H16 strain produced P(3HB-co-3HH) having the cell production of 110.4 g/L and polyester content of 73.8 wt % by culturing for 48 hours. This productivity largely exceeded the productivity of P(3HB-co-3HH) which have so far been reported. Moreover, this strain did not require antibiotics or any other selective pressures through the whole culture processes, and substantially all the cells were found to have accumulated P(3HB-co-3HH) when the culture was completed.

That is, the present invention is described as follows.

[1] A microorganism
which originally has a polyhydroxyalkanoic acid synthase gene on its chromosome, in which at least a part of said polyhydroxyalkanoic acid synthase gene is substituted with an exogenous polyhydroxyalkanoic acid synthase gene, and
produces a copolyester constituted of two or more monomer units selected from the group consisting of 3-hydroxybutyric acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytridecanoic acid, 3-hydroxytetradecanoic acid, 3-hydroxypentadecanoic acid, and 3-hydroxyhexadecanoic acid.

[2] The microorganism according to [1],
wherein the copolyester is constituted of monomer units of 3-hydroxybutyric acid and 3-hydroxyhexanoic acid.

[3] The microorganism according to [1],
wherein the microorganism originally having a polyhydroxyalkanoic acid synthase gene on the chromosome is *Ralstonia eutropha*.

[4] The microorganism according to [3],
wherein *Ralstonia eutropha* is a *Ralstonia eutropha* H16 strain.

[5] The microorganism according to [1],
wherein the exogenous polyhydroxyalkanoic acid synthase gene codes for an enzyme derived from *Aeromonas caviae* or a mutant thereof.

[6] The microorganism according to [5],
wherein the mutant is the one produced by at least one amino acid substitution (a) or (b):
(a) substitution of serine for asparagine of the 149th amino acid;
(b) substitution of glycine for aspartic acid of the 171st amino acid.

[7] The microorganism according to [1],
wherein the exogenous polyhydroxyalkanoic acid synthase gene codes for a mutant enzyme derived from *Aeromonas caviae* represented by the amino acid sequence shown under SEQ ID NO:9, which is prepared by substituting serine for asparagine of the 149th amino acid and substituting glycine for aspartic acid of the 171st amino acid.

[8] A microorganism
which is KNK-005 strain.

[9] A production method of a polyester
which comprises using the microorganism according to [1].

The copolyester according to the present invention is a copolymer constituted of two or three or more monomer units selected from the group consisting of 3-hydroxybutyric acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytridecanoic acid, 3-hydroxytetradecanoic acid, 3-hydroxypentadecanoic acid and 3-hydroxyhexadecanoic acid, among polymers comprising, as a monomer unit, 3-hydroxyalkanoic acid represented by the following general formula:

(wherein $R^1$ and $R^2$ represent an alkyl group having 1 or more carbon atom(s) and may be the same or different in the polymer; and m and n represent numbers of monomer unit of said polymer, and are 1 or more, respectively).

As the above copolyester, preferred is one constituted of the monomer units of 3-hydroxybutyric acid and 3-hydroxyhexanoic acid.

The microorganism to be used in the present invention is not particularly restricted provided that it originally, as the microbial species, has a polyhydroxyalkanoic acid synthase gene on its chromosome DNA, and includes a microorganism modified to be capable of using another carbon source, a microorganism in which production or incorporation of a substrate monomer is modified, or a microorganism modified for increasing the production. As examples thereof, there may be mentioned bacteria such as *Ralstonia* genus such as *Ralstonia eutropha* (It is identical with *Wautersia eutropha*, *Cupriavidus necator* in Taxonomy), *Aeromonas* genus such as *Aeromonas caviae*, *Alcaligenes* genus such as *Alcaligenes latus*, *Pseudomonas* genus such as *Pseudomonas aeruginosa* and *Pseudomonas putida*. In view of the safety and productivity, preferred is *Ralstonia* genus, more preferred is a *Ralstonia eutropha*, and still more preferred is a *Ralstonia eutropha* H16 strain.

Among genes derived from various PHA-accumulating organisms, the exogenous polyhydroxyalkanoic acid synthase gene to be used in the present invention is not particularly restricted provided that it can accumulate a copolyester. As such genes, there may be mentioned, for example, a polyhydroxyalkanoic acid synthase gene isolated from *Aeromonas caviae* (Fukui et al., J. Bacteriol., 179: 4821-4830 (1997)), *Nocardia corallina* (Gen Bank accession number AF019964), *Pseudomonas aeruginosa* (Timm et al. Eur. J. Biochem., 209:15-30 (1992)), *Pseudomonas oleovorans* (Huisman et al., J. Biol. Chem., 266:2191-2198 (1991)), *Thiocystis violaceae* (Liebergesell et al., Appl. Microbiol. Biotechnol., 38:493-501 (1993)), and the like. Preferred are those coding for an enzyme derived from *Aeromonas caviae* or a mutant thereof.

Moreover, it is also possible to use genes in which a part of the base sequence is modified for modifying the amino acid sequence within the range that the targeted enzymatic activity is not lost. For example, preferably used are a polyester synthase gene derived from *Aeromonas caviae* in which serine is substituted for 149th amino acid asparagine (N149S mutant gene) or a polyester synthase gene derived from *Aeromonas caviae* in which glycine is substituted for 171st aspartic acid (D171G mutant gene), both of them are described by Kichise et al. (Appl. Environ. Microbiol., 68:2411-2419 (2002)), a polyester synthase gene derived from *Aeromonas caviae* represented by the amino acid sequence shown under SEQ ID NO:9 in which both of the above-mentioned amino acid substitution are combinedly carried out, or the like.

The above genes may have a promoter and/or ribosome binding site(s), but it is not necessarily required.

The aspect of substitution of the polyester synthase gene may be any form provided that the activity of the enzyme coded by the polyester synthase gene originally occurring on the chromosome (gene before substitution) is lost and the exogenous polyester synthase gene (substituted gene) is expressed. After the substitution, all of the gene before substitution may be lost from the chromosome, or a part thereof may occur, or they may exist in the divided form. As one aspect of substitution, when the substituted gene has a ribosome binding site and does not have a promoter, it is possible to select such mode in which the substituted gene is connected to the downstream of a promoter of the gene before substitution. Moreover, as another aspect of substitution, when the substituted gene does not have a promoter and ribosome binding site, it is possible to select such mode in which the substituted gene is connected to the downstream of a ribosome binding site of the gene before substitution. The mode of substitution may be either form in which the polyester synthase protein expressed after the substitution is a single protein coded by the substituted gene or a fusion protein with a protein coded by the gene before substitution. The aspect of substitution of the polyester synthase gene used in the present invention is not restricted to those forms mentioned above, but preferably, from the initiation codon to the terminal codon of the gene before substitution are substituted with the initiation codon to the terminal codon of the substituted gene.

The process for site-specifically substitution of a gene on the chromosome is well-known to the person skilled in the art. As a typical process, there are a process comprising using transposon and a homologous recombination mechanism (Ohman et al., J. Bacteriol., 162:1068-1074 (1985)), a process principally comprising a site-specific incorporation caused by the homologous recombination mechanism and loss by homologous recombination of the second stage (Noti et al., Methods Enzymol., 154:197-217 (1987)), or the like. In addition, it is also possible to use a process comprising making sacB gene derived from *Bacillus subtilis* coexist with the substituted gene for easily isolating a microbial strain from which sacB gene is lost by homologous recombination of the second stage as a strain resistant against a sucrose-added medium (Schweizer, Mol. Microbiol., 6:1195-1204 (1992); Lenz et al., J. Bacteriol., 176:4385-4393 (1994)). However, the process is not particularly restricted provided that the gene on the chromosome can be substituted. In the following, the process for substituting a PHA synthase gene derived from *Aeromonas caviae* (phaC$_{Ac}$) for a PHA synthase gene derived from *Ralstonia eutropha* (phaC$_{Re}$) is more specifically described.

First, a substitution flagment is produced. The substitution flagment has such form in which a coding sequence (CDS: initiation codon to termination codon are included) of phaC$_{Ac}$ is connected to the upstream sequence just before CDS of phaC$_{Re}$, followed by the downstream sequence just after CDS of phaC$_{Re}$. That is, it is a DNA flagment of phaC$_{Re}$ in which CDS alone is substituted with that of phaC$_{Ac}$. The upstream sequence and downstream sequence are homologous sequences necessary for causing homologous recombination with the gene on the chromosome. Generally, the longer its length, the higher the recombination frequency becomes, but the length can be arbitrary selected since only the homologous recombination is required.

To the substitution flagment, a gene which becomes a selective marker during the gene substitution can be added. As the gene to be a selective marker, for example, genes resistant against antibiotics such as kanamycin, chloramphenicol, streptomycin and/or ampicillin, genes for complementing various nutrition requirements, and the like can be used. When *Ralstonia eutropha* is used, a gene resistant against kanamycin is suitably used.

In addition to those genes, it is also possible to add a gene for facilitating selection of a microbial strain from which a region containing the selective marker gene is lost by homologous recombination of the second stage. As such gene, sacB gene derived from *Bacillus subtilis* can be mentioned (Schweizer, Mol. Microbiol., 6: 1195-1204 (1992)). A microbial strain in which this gene is expressed is known to be incapable of growing in a sucrose-containing medium, and by growing the strain in a sucrose-containing medium, it becomes easy to select the strain from which this gene is lost.

By connecting the substitution fragment constituted of these genes to a vector which does not replicate in a host microbial strain, a plasmid for gene substitution is produced. As such vector which can be used in the genus *Ralstonia*, the genus *Pseudomonas*, or the like, there may be mentioned, for example, pUC vector, pBluescript vector or pBR322 vector, or vectors having the same replication origin as those, or the like. Moreover, it is also possible to make DNA sequences such as mob and oriT coexist, which enable conjugal transfer.

The plasmid DNA for gene substitution produced by the constitutions as mentioned above can be introduced into a microorganism such as *Ralstonia eutropha* by conventional methods such as an electroporation method or conjugal transfer method, and can be subjected to homologous recombination.

Next, a strain into which the plasmid DNA for gene substitution is inserted onto the chromosome by homologous recombination is selected. The selection can be conducted by a method based on the gene for selection which is made coexist in the plasmid DNA for gene substitution. When a kanamycin resistant gene is used, the strain can be selected from those grown in a kanamycin-containing medium.

In the next stage, the strain from which a region containing the selective marker gene is lost from the chromosome by homologous recombination of the second stage is selected. Based on the gene for selection used in the insertion, a strain which becomes incapable of growing in a kanamycin-containing medium may be selected, for instance. However, when sacB gene coexists with a plasmid for gene substitution, it can be easily selected from strains growing in a sucrose-containing medium. For confirming whether the thus selected strain is one in which a gene is substituted as to be intended, conventional methods can be used such as a PCR method, southern hybridization method, and determination of the DNA base sequence. As mentioned above, a strain in which the PHA synthase gene (phaC$_{Ac}$)

derived from *Aeromonas caviae* is substituted for the PHA synthase gene (phaC$_{Re}$) derived from *Ralstonia eutropha* can be obtained. As such strain, there may be mentioned KNK-005 strain produced in the following Example.

In the practice of the present invention, copolyesters can be accumulated within the microorganisms by proliferating the microorganism of the invention under the existence of a carbon source. As the carbon source, sugar, oils and fats, or fatty acid can be used. As the nutrition source other than the carbon source, a nitrogen source, inorganic salt source, and other organic nutrient sources can be arbitrary used.

As the sugar, there may be mentioned, for example, carbohydrates such as glucose and fructose. As the oils and fats, there may be mentioned oils and fats having 10 or more carbon atoms and containing a large amount of saturated and/or unsaturated fatty acids, for example, coconut oil, palm oil, palm kernel oil, and the like. As the fatty acid, there may be mentioned saturated and/or unsaturated fatty acids such as hexanoic acid, octanoic acid, decanoic acid, lauric acid, oleic acid, palmitic acid, linoleic acid, linolenic acid and myristic acid, or fatty acid derivatives, such as esters and salts of these fatty acids.

As the nitrogen source, there may be mentioned, for example, ammonia, ammonium salts such as ammonium chloride, ammonium sulfate and ammonium phosphate, peptone, meat extract, yeast extract, and the like.

As the inorganic salts, there may be mentioned, for example, potassium dihydrogenphosphate, dipotassium hydrogenphosphate, magnesium phosphate, magnesium sulfate, sodium chloride, and the like.

As the other organic nutrient sources, there may be mentioned, for example, amino acids such as glycine, alanine, serine, threonine and proline; vitamins such as vitamin B1, vitamin B12 and vitamin C; and the like.

The culture temperature may be any temperatures as long as the cells can grow, and preferred as this temperature is 20 to 40° C. The culture period is not particularly restricted, and may be about 1 to 10 days.

Polyesters accumulated in the obtained culture cells can be recovered by conventional methods.

Polyesters can be recovered by the following methods, for example. After completion of the culture, the cells are separated from the culture fluid using a centrifugal machine, etc., washed with distilled water, methanol, etc., and then dried. From these dried cells, polyesters are extracted using an organic solvent such as chloroform. From the polyester-containing organic solvent, cell components are removed by filtration, etc., and a poor solvent such as methanol or hexane is added to the filtrate to precipitate polyesters. Then, the supernatant fluid is removed by filtration or centrifugation, and dried. In such manner, polyesters can be recovered.

As a simple method for confirming production of polyesters, a staining method using Nile red can be used. That is, whether polyesters are produced can be confirmed by a method comprising adding Nile red to an agar medium in which recombinant cells grow, culturing the recombinant cells for 1 to 7 days, and observing whether the recombinant cells turn red or not.

According to the present invention, a recombinant microbial strain capable of stably producing a polyhydroxyalkanoic acid (PHA) at a high production rate in an industrial fermentation process can be provided, and a highly-pure polyhydroxyalkanoic acid (PHA) can be easily produced in a large amount at a low cost.

BEST MODE FOR CARRYING OUT THE INVENTION

The following examples illustrate the present invention, however, these examples are by no means limitative of the scope of the present invention.

EXAMPLE 1

Construction of a Plasmid for Gene Substitution

A PCR reaction was carried out using cells of a *Ralstonia eutropha* H16 strain as a supply source of a template DNA and using primers as shown under SEQ ID NO:1 and NO:2, and a DNA fragment containing a structural gene of polyhydroxyalkanoic acid synthase gene (phaC$_{Re}$) was obtained. The PCR reaction conditions were as follows: (1) at 94° C. for 2 minutes, (2) at 94° C. for 30 seconds, (3) at 45° C. for 30 seconds, (4) at 72° C. for 3 minutes, 25 cycles of (2) to (4), and (5) at 72° C. for 5 minutes. As a polymerase, TaKaRa LA Taq (product of TAKARA BIO INC.) was used. The DNA fragment obtained by PCR was cleaved with the restriction enzyme BamHI, and subcloned into the vector pBluescriptIIKS (-) (product of TOYOBO CO., LTD.) at the site which had already been cleaved with BamHI (pBlue-phaC$_{Re}$).

N149S/D171G mutant, which is a polyester synthase mutant gene derived from *Aeromonas caviae*, was produced as follows. First, pBluescriptIIKS (-) (product of TOYOBO CO., LTD.) was treated with PstI, blunted using DNA Blunting Kit (product of TAKARA BIO INC.), subjected to ligation, and deleted PstI site. Then, this plasmid was treated with XhoI, blunted using DNA Blunting Kit (product of TAKARA BIO INC.), subjected to ligation, and the plasmid pBlue-New from which XhoI site is deleted was obtained. To EcoRI site of this plasmid, d13 fragment cleaved from pJRD215-EE32d13 (Japanese Kokai Publication Hei-10-108682) with EcoRI was cloned (pBlue-d13). Then, a plasmid derived from clone E2-50 distributed from Institute of Physical and Chemical Research (Kichise et al., Appl. Environ. Microbiol., 68:2411-2419 (2002)) was used as a template, amplification was carried out by PCR using a set of primers shown under SEQ ID NO:3 and NO:4 and a set of primers shown under SEQ ID NO:5 and NO:6 to obtain two fragments. The conditions were as follows: (1) at 94° C. for 2 minutes, (2) at 94° C. for 30 seconds, (3) at 55° C. for 30 seconds, (4) at 72° C. for 2 minutes, 25 cycles of (2) to (4), and (5) at 72° C. for 5 minutes. The amplified two fragments were mixed in equivalent moles, and a PCR reaction was carried out again to couple said two fragments. The conditions were as follows: (1) at 96° C. for 5 minutes, (2) at 95° C. for 2 minutes, (3) at 72° C. for 1 minute, and 12 cycles of (2) to (3). As a polymerase, Pyrobest polymerase (product of TAKARA BIO INC.) was used. A DNA fragment with the objective size was extracted from an agarose electrophoresis gel, treated with PstI and XhoI, and then substituted with pBlue-d13, which had already been treated with PstI and XhoI, in order to accomplish cloning (pBlue-N149S/D171G). The base sequence was determined using DNA sequencer 310 Genetic Analyzer manufactured by PERKIN ELMER APPLIED BIOSYSTEMS, and it was confirmed as a mutant gene of the PHA synthase gene in which serine is substituted for 149th amino acid asparagines, and glycine is substituted for 171st aspartic acid. The amino acid sequence is shown under SEQ ID:9.

Using pBlue-N149S/D171G as a template, a PCR reaction was carried out using primers shown under SEQ ID NO:7 and NO:8, a structural gene DNA of N149S/D171G mutant was amplified. The PCR conditions were as follows: (1) at 94° C. for 2 minutes, (2). at 94° C. for 30 seconds, (3) at 45° C. for 30 seconds, (4) at 72° C. for 2 minutes, 25 cycles of (2) to (4), and (5) at 72° C. for 5 minutes. As a polymerase, TaKaRa LA Taq (product of TAKARA BIO INC.) was used. Then, pBlue-phaC$_{Re}$ was treated with the restriction enzymes SbfI and Csp45I, and the above-amplified DNA fragment, which had already been treated with SbfI and Csp45I, was substituted with phaC$_{Re}$ structural gene, in order to accomplish cloning (pBlue-phaC$_{Re}$:: N149S/D171G).

Next, plasmid pJRD215 (ATCC37533) was treated with the restriction enzymes XhoI and DraI to isolate a DNA fragment of about 1.3 kb containing a kanamycin resistance gene, and the resulting fragment was blunted using DNA Blunting Kit (product of TAKARA BIO INC.). This fragment was inserted into pBlue-phaC$_{Re}$::N149S/D171G at the site which had already been cleaved with the restriction enzyme SalI and then blunted in the same manner as above (pBlue-phaC$_{Re::N}$149S/D171G-Km).

Subsequently, plasmid pMT5071 (Tsuda, GENE, 207:33-41 (1998)) was treated with the restriction enzyme NotI to isolate a DNA fragment of about 8 kb containing sacB gene. The fragment was inserted into pBlue-phaC$_{Re}$::N149S/D171G-Km at the site which had already been cleaved with NotI, and the plasmid for gene substitution pBlue-phaC$_{Re::N}$149S/D171G-KmSAC was produced.

Figure 1:
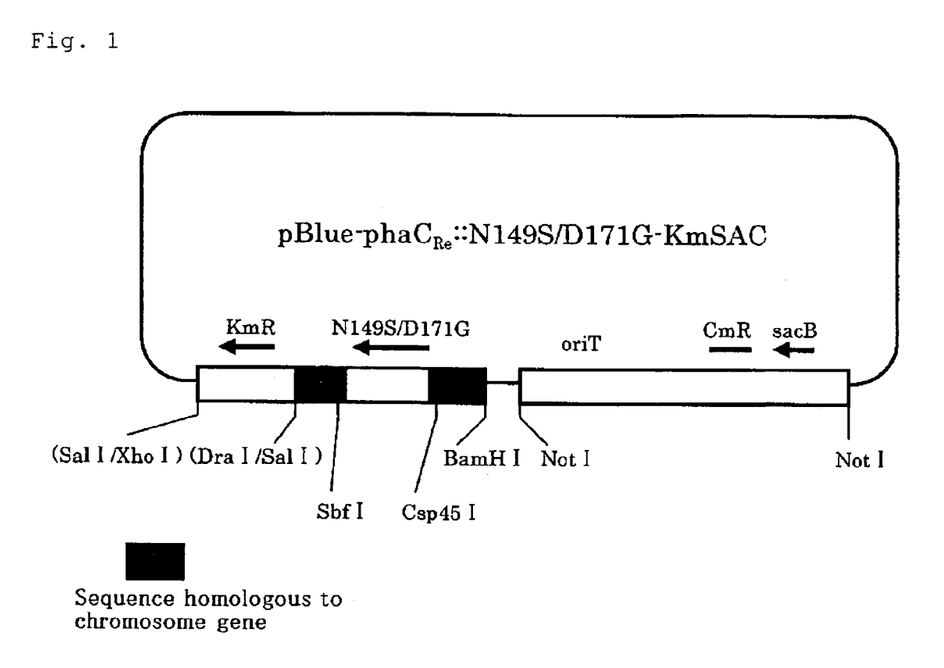
FIG. 1 is a scheme view showing the constitution of the plasmid for gene substitution pBlue-phaC$_{Re}$::N149S/D171G-KmSAC constructed in Example 1.

A scheme view showing the constitution of the plasmid for gene substitution pBlue-phaC$_{Re}$::N149S/D171G-KmSAC constructed in this Example is shown in FIG. 1.

EXAMPLE 2

Construction of a Gene-substituted Strain

An *Escherichia coli* S17-1 strain (ATCC47005) was transformed with the plasmid for gene substitution pBlue-phaC$_{Re}$::N149S/D171G-KmSAC, and subjected to mixed culture with a *Ralstonia eutropha* H16 strain on Nutrient Agar medium (product of DIFCO Laboratories) to carry out conjugal transfer. A strain grown on Simmons agar medium containing 250 mg/L of kanamycin (sodium citrate 2 g/L, sodium chloride 5 g/L, magnesium sulfate-heptahydrate 0.2 g/L, ammonium dihydrogenphosphate 1 g/L, dipotassium hydrogenphosphate 1 g/L, agar 15 g/L, pH 6.8) was selected, and a strain in which the plasmid is incorporated onto the chromosome of the *Ralstonia eutropha* H 16 strain was obtained (homologous recombination of the first stage). This strain was cultured on Nutrient Broth medium (product of DIFCO Laboratories) through two generations, and diluted and applied on Nutrient Agar medium containing 15% of sucrose. Grown strains were selected to obtain the strains from which a region containing a selective marker is lost (homologous recombination of the second stage). Moreover, by analysis using PCR, a strain in which phaC$_{Re}$ gene is substituted with N149S/D171G mutant gene was isolated. This gene-substituted strain was named KNK-005 strain, and the base sequence was determined using DNA sequencer 310 Genetic Analyzer manufactured by PERKIN ELMER APPLIED BIOSYSTEMS. It was confirmed as a strain in which from the initiation codon to terminal codon of phaC$_{Re}$ gene on the chromosome are substituted with the initiation codon to terminal codon of N149S/D171G mutant gene.

Figure 2:
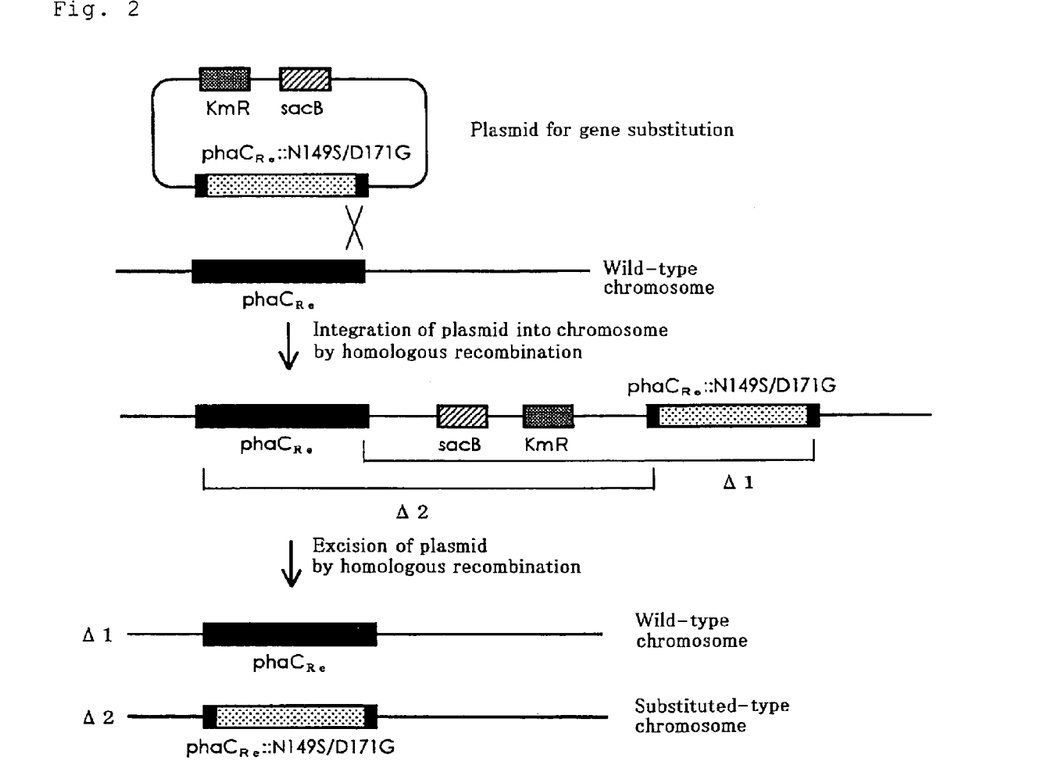
FIG. 2 is a scheme view showing the procedure of gene substitution carried out in Example 2.

The procedure of gene substitution carried out in this Example is schematically shown in FIG. 2. By homologous recombination of the first stage, the plasmid for gene substitution was integrated into the chromosome, and by homologous recombination of the second stage, the plasmid is excised from the chromosome. During homologous recombination of the second stage, depending on the site where homologous recombination occurs, the plasmid is excised together with the same substituted gene as the original one (phaC$_{Re}$::N149S/D171G in FIG. 2) (Δ1) or together with the gene before substitution (phaC$_{Re}$ in FIG. 2) (Δ2). KNK-005 strain of the present invention is obtained by homologous recombination of the second stage carried out in the location of Δ2.

EXAMPLE 3

Production and Purification of Polyester

The composition of a seed culture medium was set as follows: 1 w/v % Meat-extract, 1 w/v % Bacto-Trypton, 0.2 w/v % Yeast-extract, 0.9 w/v % Na$_2$PO$_4$.12H$_2$O, 0.15 w/v % KH$_2$PO$_4$, and pH 6.8.

The composition of a preculture medium was set as follows: 1.1 w/v % of Na$_2$PO$_4$.12H$_2$O, 0.19 w/v % of KH$_2$PO$_4$, 1.29 w/v % of (NH$_4$)$_2$SO$_4$, 0.1 w/v % of MgSO$_4$.7H$_2$O, 2.5 w/v % of palm W oleic oil, and 0.5 v/v % of solution containing trace amount of a metal salt (prepared by dissolving 1.6 w/v % of FeCl$_3$.6H$_2$O, 1 w/v % of CaCl$_2$.2H$_2$O, 0.02 w/v % of CoCl$_2$.6H$_2$O, 0.016 w/v % of CuSO$_4$.5H$_2$O, and 0.012 w/v % of NiCl$_2$.6H$_2$O in 0.1 N hydrochloric acid).

The composition of a polyester-producing medium was set as follows: 0.385 w/v % of Na$_2$PO$_4$.12H$_2$O, 0.067 w/v % of KH$_2$PO$_4$, 0.291 w/v % of (NH$_4$)$_2$SO$_4$, 0.1 w/v % of MgSO$_4$.7H$_2$O, 0.5 v/v % of solution containing trace amount of a metal salt (prepared by dissolving 1.6 w/v % of FeCl$_3$.6H$_2$O, 1 w/v % of CaCl$_2$.2H$_2$O, 0.02 w/v % of CoCl$_2$.6H$_2$O, 0.016 w/v % of CuSO$_4$.5H$_2$O, and 0.012 w/v % of NiCl$_2$.6H$_2$O in 0.1 N hydrochloric acid), and 0.05 w/v % BIOSPUREX 200K (defoaming agent: product of Cognis Japan Ltd.). As a carbon source, palm kernel oil olein, which is a low-melting point fraction prepared by fractionating palm kernel oil, was used as a single carbon source, and fed at the specific supply rate of substrate of 0.08 to 0.1 (g oils and fats)×(net weight of dry cells)$^{-1}$×(h)$^{-1}$ through the whole culture.

A glycerol stock (50 μl) of KNK-005 strain was inoculated into the seed culture medium (10 ml) and cultured for 24 hours, and the resultant was inoculated at 1.0 v/v % in a 3 L jar fermentor (product of B. E. Marubishi, Co., Ltd.; MDL-300 type) containing 1.8 L of the preculture medium. The operation conditions were as follows: culture temperature 30° C., stirring rate 500 rpm, and aeration amount 1.8 L/min. The culture was carried out for 28 hours while controlling the pH between 6.7 and 6.8. For the pH control, a 7% aqueous solution of ammonium hydroxide was used.

The polyester production culture was carried out by inoculating 5.0 v/v % of the preculture seed to a 10 L jar fermentor (product of B. E. Marubishi, Co., Ltd.; MDL-1000 type) containing 6 L of the production medium. The operation conditions were as follows: culture temperature 28° C., stirring rate 400 rpm, aeration amount 3.6 L/min, and the pH was controlled between 6.7 and 6.8. For the pH control, a 7% aqueous solution of ammonium hydroxide was used. The culture was carried out for about 48 hours. After completion of the culture, the cells were recovered by centrifugation, washed with methanol, and then freeze-dried. The weight of the dry cells was determined, and was found to be 110.4 g/L.

To about 1 g of the obtained dry cells, 100 ml of chloroform was added and the mixture was stirred at room temperature through a day and night to extract polyesters within the cells. After filtrating the cell residues, the polyesters were concentrated to about 30 ml in the total volume using an evaporator, gradually added with about 90 ml of hexane, and left for 1 hour while slowly stirring. The precipitated polyesters were filtrated, and dried in vacuum at 50° C. for 3 hours. The weight of the dry polyesters was determined and the polyester content within the cells was calculated. Consequently, the polyester content obtained by KNK-005 strain was as high as 73.8 (wt %) in 48 hours.

EXAMPLE 4

Evaluation of Stability of Polyester-producing Ability

The bacterial culture liquid obtained in Example 3 at the completion of the polyester production culture was diluted and inoculated to Nutrient Agar medium. The colonies which have grown were inoculated to a Nile red-containing medium (disodium hydrogenphosphate-dodecahydrate 9 g, potassium dihydrogenphosphate 1.5 g, ammonium chloride 0.05 g, magnesium sulfate-heptahydrate 0.02 g, fructose 0.5 g, cobalt chloride-hexahydrate 0.25 ppm, iron (III) chloride-hexahydrate 16 ppm, calcium chloride-dihydrate 10.3 ppm, nickel chloride-heptahydrate 0.12 ppm, copper sulfate-pentahydrate 0.16 ppm, Nile red 0.5 mg, and agar 15 g/1 L). After culturing the colonies at 30° C. for 3 days, those turning red can be judged as they produce polyesters. 100 colonies were evaluated, and all of the colonies were found to have the polyester-producing ability.

INDUSTRIAL APPLICABILITY

According to the present invention, a recombination microbial strain capable of stably producing a polyhydroxyalkanoic acid (PHA) at a high production rate in an industrial fermentation process can be provided, and a highly-pure polyhydroxyalkanoic acid (PHA) can be easily produced in a large amount at a low cost.

The invention claimed is:

1. An isolated microorganism which originally has a polyhydroxyalkanoic acid synthase gene in chromosome, in which at least a part of said polyhydroxyalkanoic acid synthase gene is substituted with an exogenous polyhydroxyalkanoic acid synthase gene to lose enzymatic activity of polypeptide encoded by said polyhydroxyalkanoic acid synthase gene originally in chromosome for expression of a single protein encoded by the exogenous polyhydroxyalkanoic acid synthase gene or a fusion protein with a protein encoded by the gene before substitution, and produces a copolyester constituted of two or more monomer units selected from the group consisting of: 3-hydroxybutyric acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytridecanoic acid, 3-hydroxytetradecanoic acid, 3-hydroxypentadecanoic acid, and 3-hydroxyhexadecanoic acid.

2. The isolated microorganism according to claim 1 wherein the copolyester is constituted of monomer units of 3-hydroxybutyric acid and 3-hydroxyhexanoic acid.

3. The isolated microorganism according to claim 1 wherein the microorganism originally having a polyhydroxyalkanoic acid synthase gene in chromosome is *Ralstonia eutropha*.

4. The isolated microorganism according to claim 3 wherein *Ralstonia eutropha* is a *Ralstonia eutropha* H16 strain 5. The isolated microorganism according to claim 1 wherein the exogenous polyhydroxyalkanoic acid synthase gene encodes an enzyme isolated from *Aeromonas caviae* or a mutant enzyme thereof which is the one produced by at least one amino acid substitution (a) or (b):

(a) substitution of serine for asparagine of the $149^{th}$ amino acid in polyhydroxyalkanoic acid synthase gene of *Aeromonas caviae;*

(b) substitution of glycine for aspartic acid of the $171^{st}$ amino acid in polyhydroxyalkanoic acid synthase gene of *Aeromonas caviae.*

6. The isolated microorganism according to claim 1 wherein the exogenous polyhydroxyalkanoic acid synthase gene encodes the amino acid sequence shown under SEQ ID NO:9.

7. A production method of a polyester which comprises culturing the microorganism according to claim 1 and recovering polyester from the microorganism.

8. The isolated microorganism according to claim 1, wherein the microorganism originally having a polyhydroxyalkanoic acid synthase gene in chromosome is *Ralstonia eutropha* H16 strain, the exogenous polyhydroxyalkanoic acid synthase gene encodes the amino acid sequence shown under SEQ ID NO:9, and the initiation codon to the terminal codon of polyhydroxyalkanoic acid synthase gene are substituted with the initiation codon to the terminal codon of gene encoding the amino acid sequence shown under SEQ ID NO:9.

* * * * *

```
                          SEQUENCE LISTING

<160> NUMBER OF SEQ ID NOS: 9

<210> SEQ ID NO 1
<211> LENGTH: 27
<212> TYPE: DNA
<213> ORGANISM: Artificial Sequence
<220> FEATURE:
<223> OTHER INFORMATION: Chemically-synthesized PCR Primer

<400> SEQUENCE: 1
gtcggatccc gggcaagtac cttgccg                                    27

<210> SEQ ID NO 2
<211> LENGTH: 27
<212> TYPE: DNA
<213> ORGANISM: Artificial Sequence
<220> FEATURE:
<223> OTHER INFORMATION: Chemically-synthesized PCR Primer

<400> SEQUENCE: 2
gacggatcca tggtgtcgac cagcttg                                    27

<210> SEQ ID NO 3
<211> LENGTH: 26
<212> TYPE: DNA
<213> ORGANISM: Artificial Sequence
<220> FEATURE:
<223> OTHER INFORMATION: Chemically-synthesized PCR Primer

<400> SEQUENCE: 3
aggttctggc cgccggactc cagggt                                     26

<210> SEQ ID NO 4
<211> LENGTH: 32
<212> TYPE: DNA
<213> ORGANISM: Artificial Sequence
<220> FEATURE:
<223> OTHER INFORMATION: Chemically-synthesized PCR Primer

<400> SEQUENCE: 4
```

```
ggagagcata tgagccaacc atcttatggc cc                              32

<210> SEQ ID NO 5
<211> LENGTH: 26
<212> TYPE: DNA
<213> ORGANISM: Artificial Sequence
<220> FEATURE:
<223> OTHER INFORMATION: Chemically-synthesized PCR Primer

<400> SEQUENCE: 5
accctggagt ccggcggcca gaacct                                     26

<210> SEQ ID NO 6
<211> LENGTH: 55
<212> TYPE: DNA
<213> ORGANISM: Artificial Sequence
<220> FEATURE:
<223> OTHER INFORMATION: Chemically-synthesized PCR Primer

<400> SEQUENCE: 6
atggatcctg cagttagtgg tggtggtggt ggtgtgcggc gtcctcctct gttgg     55

<210> SEQ ID NO 7
<211> LENGTH: 63
<212> TYPE: DNA
<213> ORGANISM: Artificial Sequence
<220> FEATURE:
<223> OTHER INFORMATION: Chemically-synthesized PCR Primer

<400> SEQUENCE: 7
gccggttcga atagtgacgg cagagagaca atcaaatcat gagccaacca tcttatggcc  60
cgc                                                              63

<210> SEQ ID NO 8
<211> LENGTH: 83
<212> TYPE: DNA
<213> ORGANISM: Artificial Sequence
<220> FEATURE:
<223> OTHER INFORMATION: Chemically-synthesized PCR Primer

<400> SEQUENCE: 8
gggaacctgc aggcctgccg gcgccgtgca tgacgcacgc cggcactcat gcaagcgtca  60
tgcggcgtcc tcctctgttg ggc                                        83

<210> SEQ ID NO 9
<211> LENGTH: 594
<212> TYPE: PRT
<213> ORGANISM: Aeromonas caviae
<220> FEATURE:
<223> OTHER INFORMATION: variant of polyhydroxyalkanoate synthetic
      enzyme

<400> SEQUENCE: 9
```

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala

-continued

```
             65                  70                  75                  80
Gly Gln Pro Ser Glu Pro Val Ile Thr Pro Glu Arg Ser Asp Arg Arg
                 85                  90                  95
Phe Lys Ala Glu Ala Trp Ser Glu Gln Pro Ile Tyr Asp Tyr Leu Lys
            100                 105                 110
Gln Ser Tyr Leu Leu Thr Ala Arg His Leu Ala Ser Val Asp Ala
            115                 120                 125
Leu Glu Gly Val Pro Gln Lys Ser Arg Glu Arg Leu Arg Phe Phe Thr
        130                 135                 140
Arg Gln Tyr Val Ser Ala Met Ala Pro Ser Asn Phe Leu Ala Thr Asn
145                 150                 155                 160
Pro Glu Leu Leu Lys Leu Thr Leu Glu Ser Gly Gly Gln Asn Leu Val
                165                 170                 175
Arg Gly Leu Ala Leu Ala Glu Asp Leu Glu Arg Ser Ala Asp Gln
            180                 185                 190
Leu Asn Ile Arg Leu Thr Asp Glu Ser Ala Phe Glu Leu Gly Arg Asp
                195                 200                 205
Leu Ala Leu Thr Pro Gly Arg Val Val Gln Arg Thr Glu Leu Tyr Glu
        210                 215                 220
Leu Ile Gln Tyr Ser Pro Thr Thr Glu Thr Val Gly Lys Thr Pro Val
225                 230                 235                 240
Leu Ile Val Pro Pro Phe Ile Asn Lys Tyr Tyr Ile Met Asp Met Arg
                245                 250                 255
Pro Gln Asn Ser Leu Val Ala Trp Leu Val Ala Gln Gly Gln Thr Val
            260                 265                 270
Phe Met Ile Ser Trp Arg Asn Pro Gly Val Ala Gln Ala Gln Ile Asp
                275                 280                 285
Leu Asp Asp Tyr Val Val Asp Gly Val Ile Ala Ala Leu Asp Gly Val
        290                 295                 300
Glu Ala Ala Thr Gly Glu Arg Glu Val His Gly Ile Gly Tyr Cys Ile
305                 310                 315                 320
Gly Gly Thr Ala Leu Ser Leu Ala Met Gly Trp Leu Ala Ala Arg Arg
                325                 330                 335
Gln Lys Gln Arg Val Arg Thr Ala Thr Leu Phe Thr Thr Leu Leu Asp
            340                 345                 350
Phe Ser Gln Pro Gly Glu Leu Gly Ile Phe Ile His Glu Pro Ile Ile
        355                 360                 365
Ala Ala Leu Glu Ala Gln Asn Glu Ala Lys Gly Ile Met Asp Gly Arg
        370                 375                 380
Gln Leu Ala Val Ser Phe Ser Leu Leu Arg Glu Asn Ser Leu Tyr Trp
385                 390                 395                 400
Asn Tyr Tyr Ile Asp Ser Tyr Leu Lys Gly Gln Ser Pro Val Ala Phe
                405                 410                 415
Asp Leu Leu His Trp Asn Ser Asp Ser Thr Asn Val Ala Gly Lys Thr
                420                 425                 430
His Asn Ser Leu Leu Arg Arg Leu Tyr Leu Glu Asn Gln Leu Val Lys
            435                 440                 445
Gly Glu Leu Lys Ile Arg Asn Thr Arg Ile Asp Leu Gly Lys Val Lys
        450                 455                 460
Thr Pro Val Leu Leu Val Ser Ala Val Asp Asp His Ile Ala Leu Trp
465                 470                 475                 480
Gln Gly Thr Trp Gln Gly Met Lys Leu Phe Gly Gly Glu Gln Arg Phe
                485                 490                 495
```

-continued

```
Leu Leu Ala Glu Ser Gly His Ile Ala Gly Ile Ile Asn Pro Pro Ala
            500             505              510

Ala Asn Lys Tyr Gly Phe Trp His Asn Gly Ala Glu Ala Glu Ser Pro
        515             520              525

Glu Ser Trp Leu Ala Gly Ala Thr His Gln Gly Gly Ser Trp Trp Pro
    530              535              540

Glu Met Met Gly Phe Ile Gln Asn Arg Asp Glu Gly Ser Glu Pro Val
545              550              555              560

Pro Ala Arg Val Pro Glu Glu Gly Leu Ala Pro Ala Pro Gly His Tyr
             565              570              575

Val Lys Val Arg Leu Asn Pro Val Phe Ala Cys Pro Thr Glu Glu Asp
             580             585              590

Ala Ala
```